United States Patent [19]

Bisgaard

[11] Patent Number: 5,387,221
[45] Date of Patent: Feb. 7, 1995

[54] SET OF TOOLS FOR SUTURING IN DEEP SURGICAL APERTURES OR BODY CAVITIES

[76] Inventor: Therkel Bisgaard, Ahornvej 3, DK-8370 Hadsten, Denmark

[21] Appl. No.: 87,762
[22] PCT Filed: Jan. 14, 1992
[86] PCT No.: PCT/DK92/00010
§ 371 Date: Jul. 13, 1993
§ 102(e) Date: Jul. 13, 1993
[87] PCT Pub. No.: WO92/12674
PCT Pub. Date: Aug. 6, 1992

[30] Foreign Application Priority Data

Jan. 17, 1991 [DK] Denmark .............. 0081/91

[51] Int. Cl.⁶ ............................................. A61B 17/00
[52] U.S. Cl. ............................ 606/148; 606/139; 606/147; 112/80.03; 112/169; 289/17
[58] Field of Search ............... 606/139, 144, 145, 147, 606/148, 151; 112/169, 80.03

[56] References Cited

U.S. PATENT DOCUMENTS

| 671,337 | 4/1901 | Gibson | 606/148 |
| 2,646,045 | 7/1953 | Priestley | 606/144 |
| 3,139,089 | 6/1964 | Schwerin | 606/147 |
| 3,168,097 | 2/1965 | Dormia | 606/147 |
| 3,871,379 | 3/1975 | Clarke | 606/148 |
| 3,946,740 | 3/1976 | Bassett . | |
| 4,164,225 | 8/1979 | Johnson et al. | 606/145 |
| 4,545,374 | 10/1985 | Jacobson | 606/207 |
| 4,621,640 | 11/1986 | Mulhollan et al. | 606/144 |
| 4,674,501 | 6/1987 | Greenberg | 606/205 |
| 4,935,027 | 6/1990 | Yoon . | |
| 5,037,433 | 8/1991 | Wilk et al. | 606/144 |
| 5,176,691 | 1/1993 | Pierce | 606/148 |

FOREIGN PATENT DOCUMENTS

0509640 10/1930 Germany .............. 606/127

Primary Examiner—Stephen C. Pellegrino
Assistant Examiner—Jeffrey A. Schmidt
Attorney, Agent, or Firm—Watson, Cole, Grindle & Watson

[57] ABSTRACT

A needle driving device (1) includes a pivotally mounted needle holder (3) for a curved suturing needle (12). Following the initial pivot the needle driving member (16) is actuated for pushing the needle out of the holder. The pointed end of the needle (14) is thereby pushed to the surface of the sutured tissue. The needle is drawn outside the aperture by a pair of tongs and a surgeon may bind an initial knot on the thread. Slots (51) arranged at the ends of two V-shaped prongs enable the knot to come into contact with the tissue. The knot is then completed and brought into contact with the tissue. As the thread guides are separated an outward pull is effected which makes it possible to tie a knot even in very deep surgical apertures.

10 Claims, 6 Drawing Sheets

SET OF TOOLS FOR SUTURING IN DEEP SURGICAL APERTURES OR BODY CAVITIES

BACKGROUND OF THE INVENTION

The present invention relates to a set of tools for suturing in deep surgical apertures or body cavities and comprising: a needle driving device having an elongated needle holder support member and a needle holder with a channel for accommodating a curved surgical needle provided with a thread, which needle holder is arranged at one end of the elongated needle holder support member which comprises an elongated member with a flexible foremost end for driving the needle out of the needle holder, and a gripping member, e.g. a pair of tongs, for gripping and extracting the needle into a position outside the surgical aperture or body cavity.

Up to now, it has been difficult to perform a suturing in deep surgical apertures or in deep body cavities. A manuel insertion of suturing needles has ordinarily been effected by means of a pair of tongs or special needle holders. This has necessitated the formation of large surgical apertures in order to have sufficient space to insert the needle through the tissue in the position desired in order to arrange the thread in a correct manner.

Different kinds of tools for suturing in deep surgical apertures or body cavities are known. An example is known from U.S. Pat. No. 3,946,740. The tool described is a tong-like instrument which makes it possible to suture in a region in which a surgeon will have difficulties in inserting the needle through the tissue to be sutured. From U.S. Pat. No. 4,935,027 a thread conducting member is known which comprises a tubular structure being slotted. This member is rather voluminous and difficult to use in small apertures.

However, the prior art tool requires that the tissues to be sutured are maintained so as to position them correctly for clamping between the two jaws of the tong-like tool. The tissue should be flap-formed so as to allow them to be arranged between the jaws which contain a needle driving instrument and a gripping member, respectively for gripping and extracting the needle after its passage through the tissue.

The suturing tool described can only be used in surgical apertures into which surgeons have a direct access and which have a sufficient size to allow other auxiliary instruments to be introduced to maintain the tissue in position. Thus, it is a drawback of the suturing tool described that it only has a limited area of use.

It is the object of the present invention to provide a tool of the type described in the introductory part which allows a surgeon to suture in smaller regions or through smaller apertures than it has previously been possible.

According to the present invention this object is achieved with a set of tools which is characterized in that the needle holder is mounted pivotally at said one end of the elongated needle holder support member, that actuating means for pivoting the needle holder and the flexible foremost end of the needle driving member are provided at the other end of the elongated needle holder support member, that the set of tools further comprises a thread conducting member having an elongated thread guide support member with two prongs arranged in V-shape arranged at one end of the elongated thread guide support member which at its other end is provided with a handle and that thread guides are constituted by means in the free end of each of the prongs.

Due to the elongated support members which may be flexible or rigid members, the set of tools according to the present invention permits an operation in deep surgical apertures or body cavities. The depth of the surgical aperture is solely determined by the length of the elongated support members. As the needle holder is pivotally mounted at the one end of the elongated needle holder support member, it becomes possible to introduce a curved needle without requiring a flap-formed shape of the tissues to be sutured.

The pivoting of the needle holder is actuated from the other end of the elongated needle holder support member. This allows the needle holder having the point of the needle positioned immediately outside the curved channel to be introduced into the tissue at one side of the opening or wound to be sutured. Through the pivoting, the initial introduction of the needle will be effected in a direction substantially perpendicularly to the surface of the tissue. During the initial pivoting the needle is conducted through a circular path in direction towards the opening to be sutured. When the point of the needle has been pivoted through an initial part of the path, the remaining movement of the needle is effected by means of the needle driving member contained in or constituting a part of the needle holder support member.

When actuating the needle driving member, the needle will, due to its curved form, continue its travel along a curved path through the tissue at the other side of the opening to be sutured until the needle has been pushed completely out of the needle holder. At this stage at least the point of the needle will be conducted to a position above the tissue. In this position the needle may be gripped by gripping members and then pulled out into a position outside the surgical aperture or the body cavity. After the needle has been pulled outside the surgical aperture, the connected suture thread and the free end of the suture thread will be situated outside the surgical aperture.

This implies that the thread should always have such a length that both ends can hang freely outside the surgical aperture or the body cavity irrespective of its depth. The gripping member may be built together with the needle driving tool or may be constituted by a separate pair of tongs.

Then the thread conducting member is used. An initial knot is made by conducting the two ends of the thread around each other outside the surgical aperture. The initial knot is subsequently pushed closely into the tissue, the two separate thread guides in the free end of each of the prongs being placed at each side of the initial knot on the part of the thread facing towards the free ends. As a result, the thread conducting member may push the partial knot completely into the tissue. The thread conducting member is then pulled out and the ends of the thread are once again conducted around each other in order to complete a knot. The two separate thread guides are then again arranged on the free ends of the thread and the further binding of the thread is conducted down into the tissue in which a final knot is formed which is tightened by pushing the thread guides forwards while at the same time exerting a backwards pull in the two thread ends. As the thread guides are separated this will cause a tightening of the knot due to a substantially opposite directed pull in each of the two ends of the thread. Then the thread may be cut immediately outside the knot either by means of a separate pair of scissors or by means of cutting members which may be actuated from outside and which are connected to the thread conducting member in close proximity to the thread guides.

The set of tools according to the present invention may be used in connection with commonly known flexible scopes. The tool e.g. makes it possible to effect a suturing in the stomach by means of a modified gastroscop which is arranged to accomodate a set of tools according to the invention. When flexible support members are used, these are preferably provided in the form of one or several tubular hollow casings containing one or several casings or wires used for performing the different work procedures by operating the actuating means via a handle outside the surgical wound. Thus, the different casings and wires are mutually displacable. Inside the casing light sources and optical instruments may also be arranged so as to allow the surgeon to monitor the suturing from the outside.

When rigid substantially rectilinear support members are used, these members may also be constituted by one or several mutually displacable casings which both are connected to actuating means in a handle and to the movable parts of the tools.

Irrespective of which embodiment is used it is necessary that the outermost end of the needle driving member is flexible so as to allow it to follow the curved channel in the needle holder when the needle is to be pushed completely out of said needle holder.

As mentioned above the thread conducting member may optionally be provided with cutting members arranged in close proximity to each thread guide. The cutting members may preferably be provided in the form of a pivotal cutter coacting with a counter cutter in the slot or the eye of the thread guide. Via connecting members the pivotal cutters are connected to an actuating bottom in the handle of the thread conducting members. The application of such cutting members may be omitted in a thread conducting member of the type manufactured with a rigid support member. This is possible as it most often will be possible to cut the two ends of the thread by means of a pair of scissors, even in relatively deep surgical apertures. Vice versa the cutting members will be advantageous in connection with thread conducting members having particularly long, flexible support members. It will be time-consuming to have to pull out the thread conducting member and then introduce a succeeding separate cutting member through a very long support member.

Thus the set of tools according to the invention will does not replace any prior art set of tools. On the contrary, the set of tools constitutes a supplement to prior art suturing tools. The set of tools makes it possible to perform an operation which up to now has been considered impossible, e.g. ruptured eardrums. The set of tools may also be used to facilitate operations in the knee, e.g. when suturing the foremost ligamenta cruciata.

In practice, the set of tools according to the invention may be introduced through tubular channels having a diameter of no more than 8–9 mm or even smaller depending on the size of the needle used. It is noted that each of the tools requires an introduction aperture having a relative large height and small width. Accordingly, a tubular channel will have room for light sources and optical instruments on each side of the tools.

DESCRIPTION OF THE DRAWINGS

The invention will now be further explained with reference to the accompanying drawings, wherein.

Figure 1:
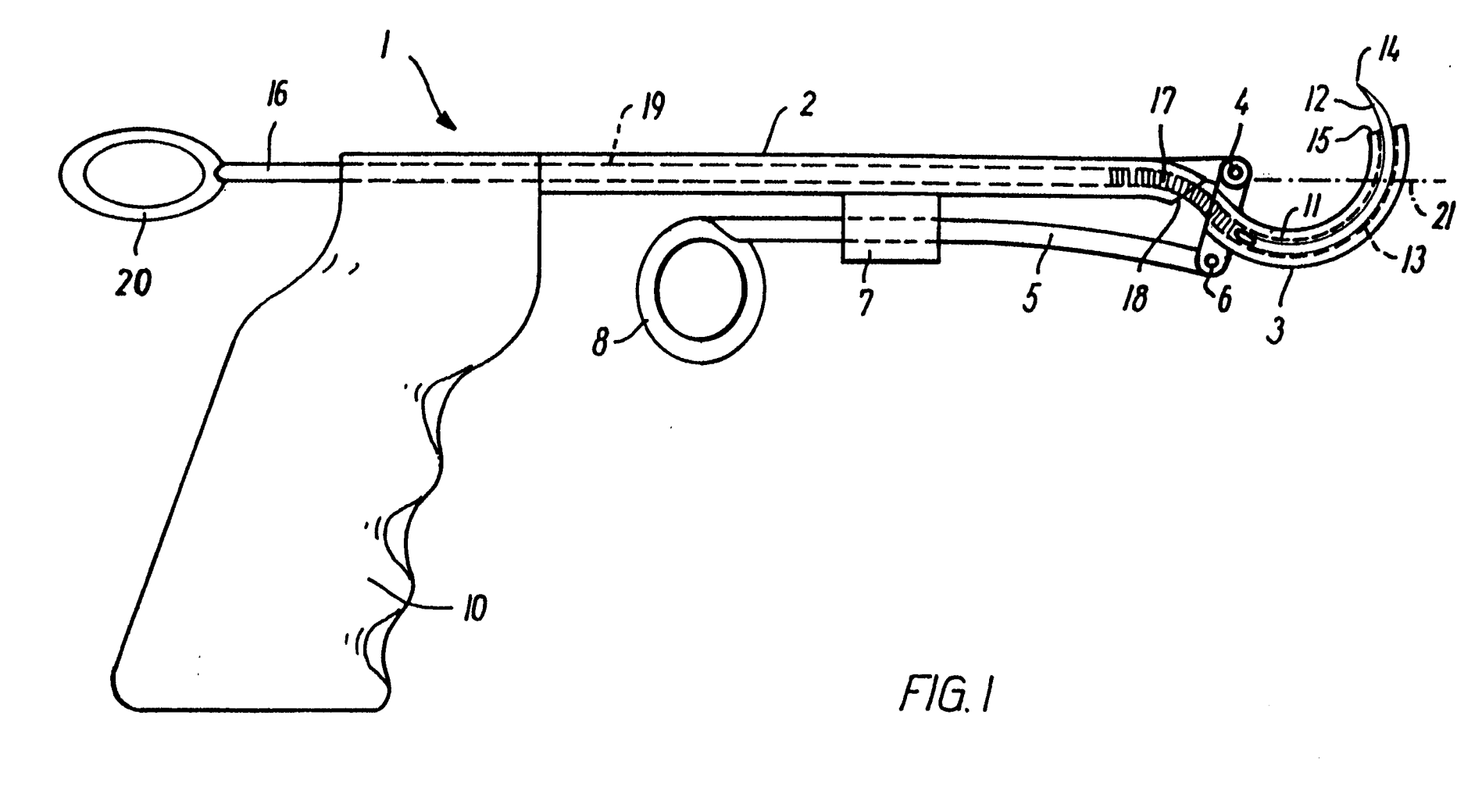
FIG. 1 is a side view of a fundamental construction of a needle driving device according to the invention.

FIG. 1 shows a needle driving device 1 for use in open surgical wounds in which surgeons are able to see what kind of operation has to be performed. The needle driving device 1 comprises an elongated substantially rectilinear support 2 for a curved needle holder 3. The needle holder 3 is pivotally mounted on the needle holder support 2 through a joint 4. In the embodiment illustrated the needle holder 3 is actuated by a rod 5 which is pivotally mounted at 6 and which is connected to the needle holder support through a bracket 7. The rod 5 is actuated by means of an eye 8 which is located in close proximity to a handle 10 of the needle driving device 1 and which is firmly connected to the needle holder support 2. The needle holder 3 is provided with a slot 11 through which a thread 28 (see FIG. 3) is arranged, said thread being connected to a needle 12. It is noted that the slot 11 may optionally be omitted by a suitable dimensioning of the curved channel in which the needle is contained in the needle holder 3. The pointed end 14 of the needle may optionally be arranged immediately inside the free end 15 of the needle holder or immediately outside the free end 15 of the needle holder 3 as illustrated in FIG. 1.

The neddle holder support 2 is tubular and contains a rod 16 which is flexible at least at the foremost end 17 in order to follow a curvature 18 of a bore 19 through the needle holder support 2. A curvature is located in close proximity to the curved needle holder 3 which has a curvature corresponding to the curvature of the needle 12 used. At its opposite end the rod 16 is provided with an eye 20 in close proximity to the handle 10. Thus, the eye 20 is intended to be actuated by the thumb of the user. When pushing the rod 16 inwards, the foremost flexible part 17 will follow the curved channel 13 in the needle holder 3 and push the needle 12 completely or partly out of the needle holder 3. This is possible when the needle holder 3 has been pivoted to the illustrated extreme position in which the foremost end 15 of the needle holder 3 is located at one side of an imaginary extension 21 of the needle holder support 2. By means of the eye 8 the needle holder 3 may be pivoted downwards into another extreme position in which the needle driving device is ready for use, and in which the foremost end 15 of the needle holder located at the opposite side of the imaginary extension 21.

It is noted that during use the needle holder does not necessarily have to be pivoted past the imaginary extension 21. In practice, a suturing may be effected even if the needle holder 3 is only pivoted through a first portion of its path towards the extreme position illustrated in FIG. 1.

As examples of dimensions of the needle holder illustrated in FIG. 1 the length of the needle holder support 2 may be approximately 250–300 mm, and the bore 19 may be approximately 1.5 mm, the diameter of the curved needle may be from approximately 8–30 mm and the width of the slot 11 may be approximately 0.5 mm. However, it is noted that the dimensions may vary within very wide limits and may highly depend on the intended use. Moreover, it is noted that the actuating member for pivoting the needle holder 3 may be embodied as a casing arranged inside or outside the needle holder support 2.

Figure 2:
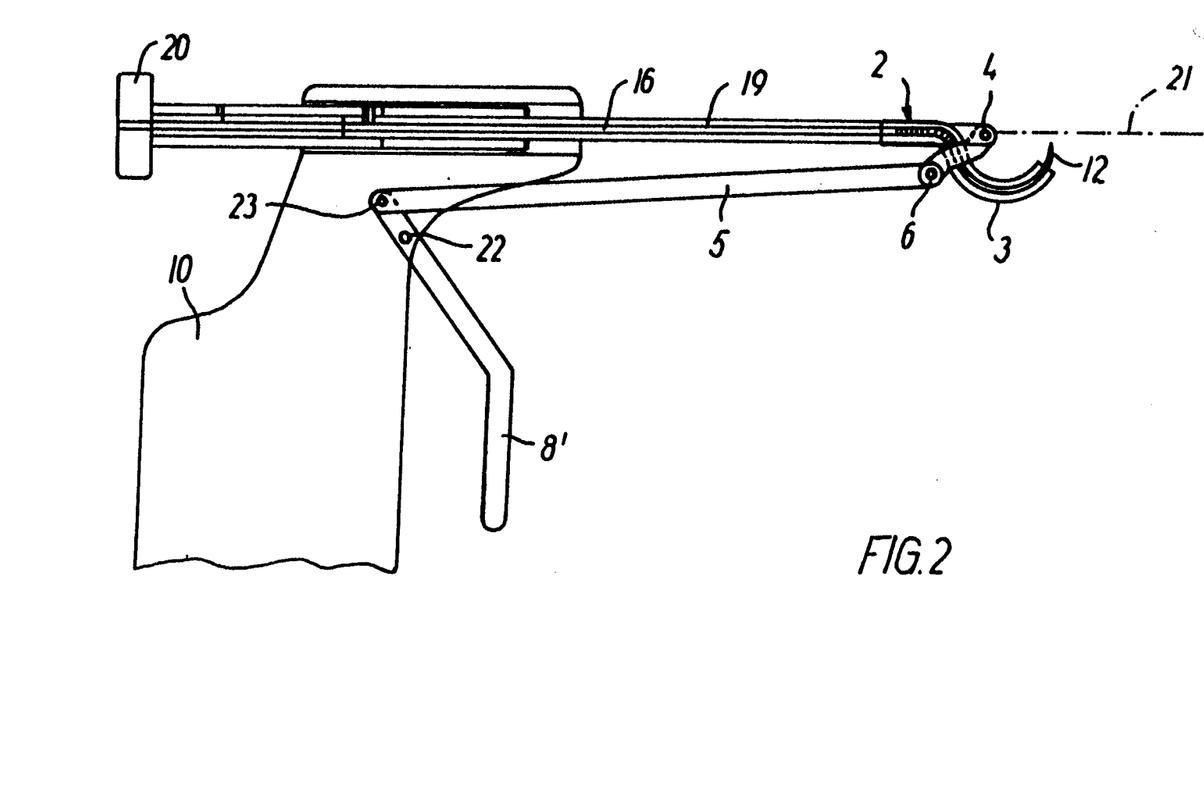
FIG. 2 is a side view of a second embodiment of a needle driving device according to the invention.

FIG. 2 illustrates another embodiment of a needle driving device. In FIG. 2 the same reference numerals are used for identical or corresponding elements. FIG. 2 illustrates a different way to actuate the pivoting of the needle holder 3 by means of a finger grip 8' which is rotatably mounted on a handle 10 on a pivot 22. The finger grip 8' is pivotally connected to a rod 5 through a joint 23. Moreover, the embodiment illustrated in FIG. 2 differs from that illustrated in FIG. 1 in that the needle holder 3 and the needle 12 are in a starting position at one side of the imaginary extension 21. In the position illustrated in FIG. 2 the needle holder 3 of the needle driving device should be pivoted approximately 20° backwards before it is ready for initial introduction of the needle 12 into a tissue. This introduction will be effected with the needle 12 orientated substantially parallelly with the extension 21 during the initial part of the introduction which is effected through the pivoting the needle holder and the needle.

Figure 3:
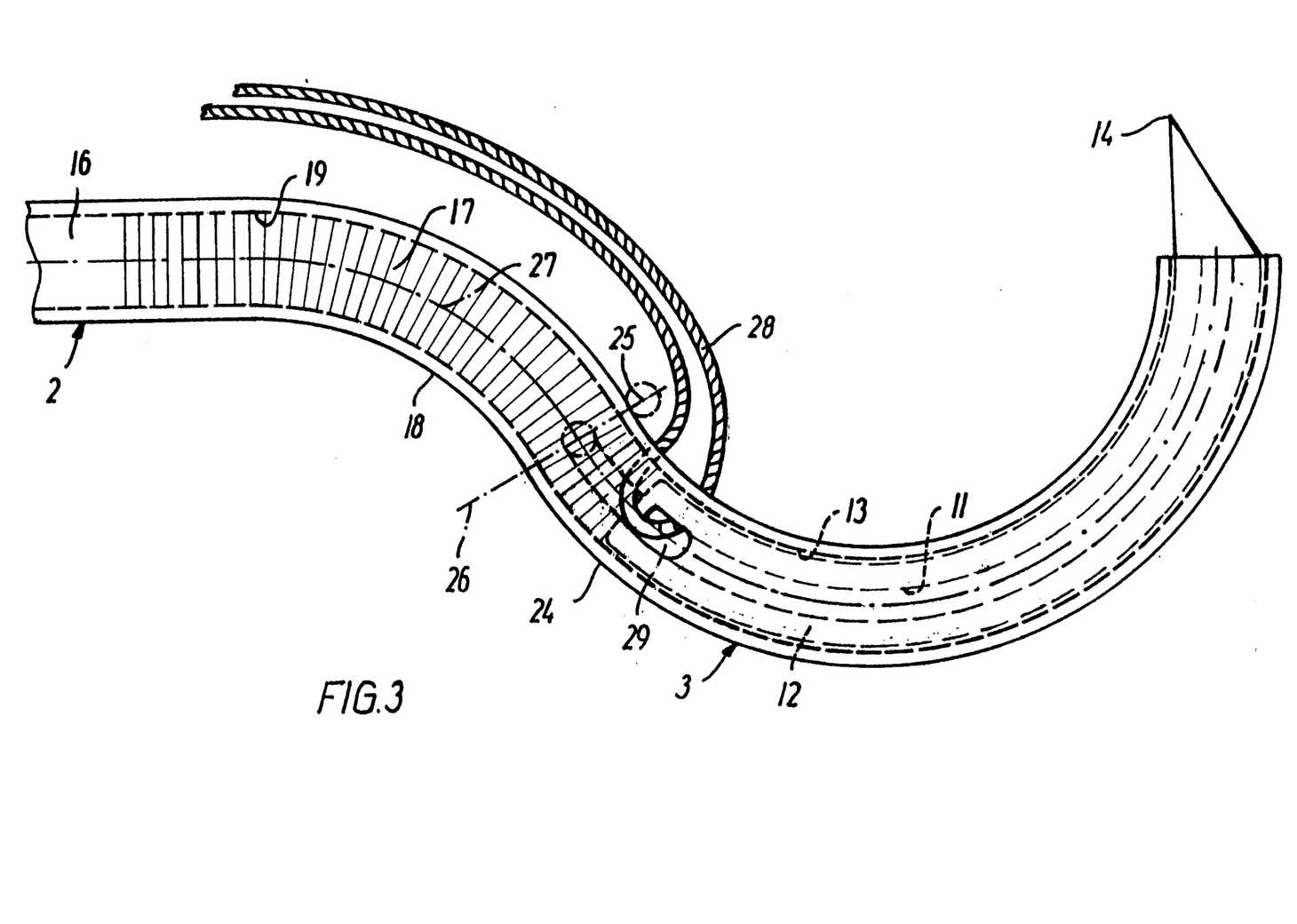
FIG. 3 is an enlarged partial side view illustrating a needle holder comprising a needle provided with a thread for use in a needle driving device according to the invention.

FIG. 3 illustrates more detailed an embodiment in which the outermost free end of the bore 19 has a curvature 19 having a radius of curvature corresponding substantially to the radius curvature of the adjacent part 24 of the needle holder 3. Moreover, it is seen that the axis 25 passing through the pivot 4 around which the needle holder 3 pivots is located in a plane 26 extending perpendicularly to the centre line 27 through the channel 19 and the channel 13 of the needle holder 3. Moreover, it is seen that the axis 25 is located immediately outside the channel, but it will also be possible to place the pivot axis 25 at the centre line 27 proper. Thus, it becomes possible to mimimize the deformations occurring in the flexible portion 17 of the driving member 16.

It is noted that FIG. 3 illustrates an advantageous situation in which the plane 26 crosses the centre line 27 in a point in which the latter has an inflexion. This will further mimimize the deformations occuring in the flexible member.

It is noted that the connection between the pivotable needle holder 3 and the needle holder support 2 may be located at another point than the one illustrated in FIG. 3, and that the outermost part of the bore 19 through the needle holder support 2 may be rectilinear.

In FIG. 3, 28 illustrates a thread positioned through an eye 29 in the blunt end of the needle 12. However, it is noted that it is also possible to use a needle in which the thread 28 is mounted directly in the blunt end. Moreover, the set of tools according to the invention may also be used, even if the thread is arranged at the pointed end 14 of the needle 12.

Figure 4:
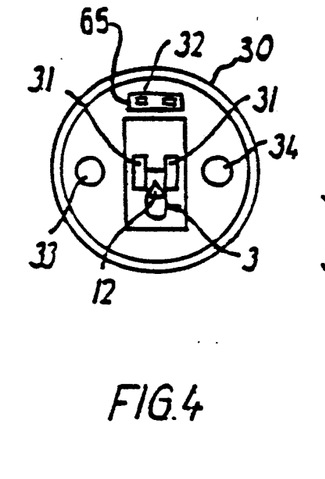
FIG. 4 is a view, seen from the end, of a further embodiment of a needle driving device according to the invention.
Figure 5:
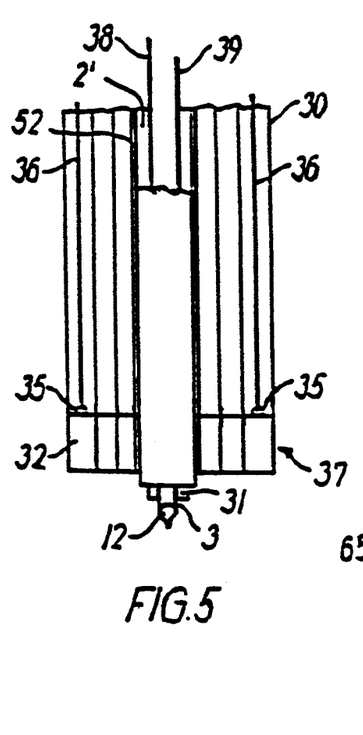
FIG. 5 is a partial sectional view through the needle driving device illustrated in FIG. 4.
Figure 6:
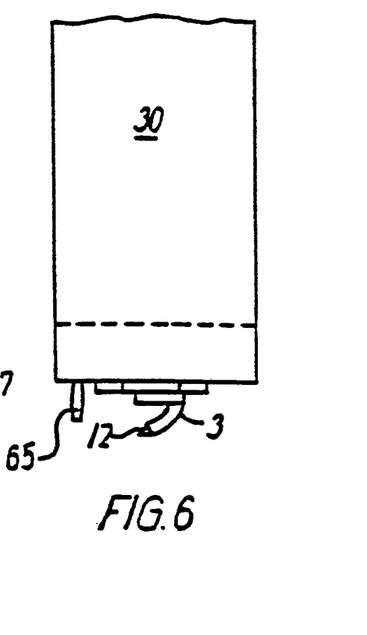
FIG. 6 is a side view of the needle driving device illustrated in FIG. 5 rotated 90°.

FIGS. 4–6 are different views illustrating a needle driving device being built into a scope and which consequently contains an elongated flexible support member 2' arranged inside a flexible pliable outer tube 30.

FIG. 4 illustrates that the needle holder 3 is pivotally mounted in two flanges 31. The way in which the needle is pivoted is not illustrated in details as this may be effected in a way corresponding to that one described in connection with FIGS. 1–3 or in another manner which would be obvious to a skilled in the art when an elongated flexible connection is used between the needle and the actuating means in the form of a handle, a finger grip and the like and the needle proper. FIG. 4 illustrates a plate 32 in which an optical instrument 33 and a light source 34 are arranged making it possible to effect a suturing at a place where a surgeon would not have immediate access. This may e.g. be in the stomach. A gripping member 65 and an end view of its gripping claws are also shown in FIG. 4. The gripping member 65 is built together with the needle driving member and has a common elongated support member.

FIG. 5 illustrates how the plate 32 is mounted in the casing 30. Through eyes 35 the plate 32 is connected to wires 36 making it possible to control the free end 37 of the scope. The needle holder support 2' is arranged inside an inner channel 52 and in such a way that it may be displaced in relation to the plate 32. In the embodiment illustrated the needle holder support 2' is hollow and contains wires 38, 39 for actuating the pivoting of the needle holder 3 and for actuating the flexible needle driving member which conducts the needle completely or partly out of the needle holder 3. FIG. 6 illustrates how the needle 12 may be pivoted outside the casing 30. The gripping member 65 is built together with the needle driving member and has a common elongated support member. The gripping claw end of the gripping member is shown in FIG. 6.

Figures 7, 8:
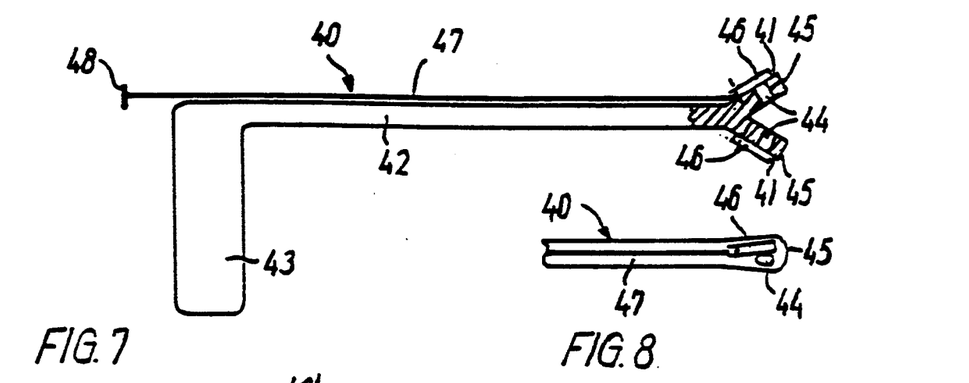
FIG. 7 is a partial, sectional view of a first embodiment of a thread conducting member according to the invention.
FIG. 8 is a partial side view of a thread conducting member illustrated in FIG. 7 rotated 90°.

FIGS. 7 and 8 illustrate a thread conducting member comprising two thread guides 41 and an elongated flexible pliable thread guide support member 42. The thread conducting member illustrated in FIGS. 7 and 8 is primarily intended to be used together with the needle driving device illustrated in FIGS. 4–6.

The thread guides 41 consist of two separate thread guides 41 arranged at one end of the elongated thread guide support member 42 which is provided with a handle 43 at the other end. In the embodiment shown the two thread guides consist of two eyes 44 arranged in separate prongs 45 arranged in a V-shape at the end of the thread guide support member 42. Moreover, the illustrated thread conducting member is provided with two pivotably mounted knives 46. By means of a connecting member connected to an actuating member 48 in close proximity to the handle 43 these knives may be actuated to co-act with the eyes 44 in cutting a thread directed through each of the eyes 44. The use of the knives 46 is optional, but is particularly advantageous in the embodiment illustrated in FIGS. 7 and 8.

Figures 9, 10:
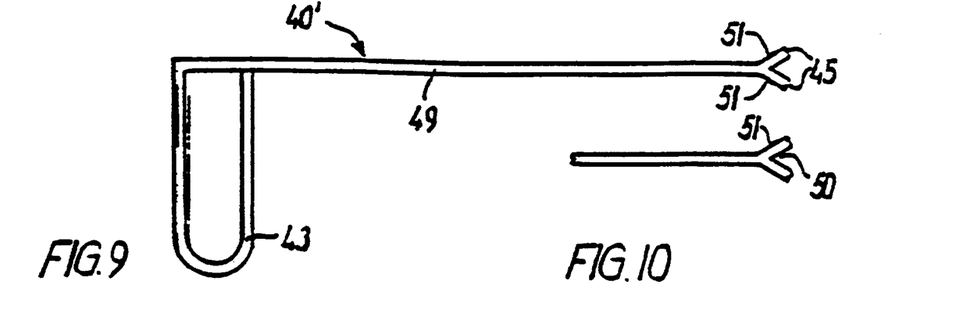
FIG. 9 is a side view of a further embodiment of a thread conducting member according to the invention.
FIG. 10 is a partial side view of the thread conducting member illustrated in FIG. 9 rotated 90°.

FIGS. 9 and 10 illustrate another embodiment of a thread conducting member 40' comprising a rigid and substantially rectilinear thread guide support member 49. The thread conducting member 40' illustrated in FIGS. 9-10 is primarily intended to be used together with a needle driving device of the type illustrated in FIGS. 1-3, e.g. in the situation where the surgeon has the possibility of looking directly into the surgical aperture. The two separate thread guides are constituted by a slot 50 formed at the free end of each of the two prongs 51 arranged in a V-shape at the end of the thread guide support member 49. In the same way as the eyes 44 the slots 50 are dimensioned in such a way that a suture thread may be placed freely displacable in the slots 50 and the eyes 44, respectively.

Figure 11:
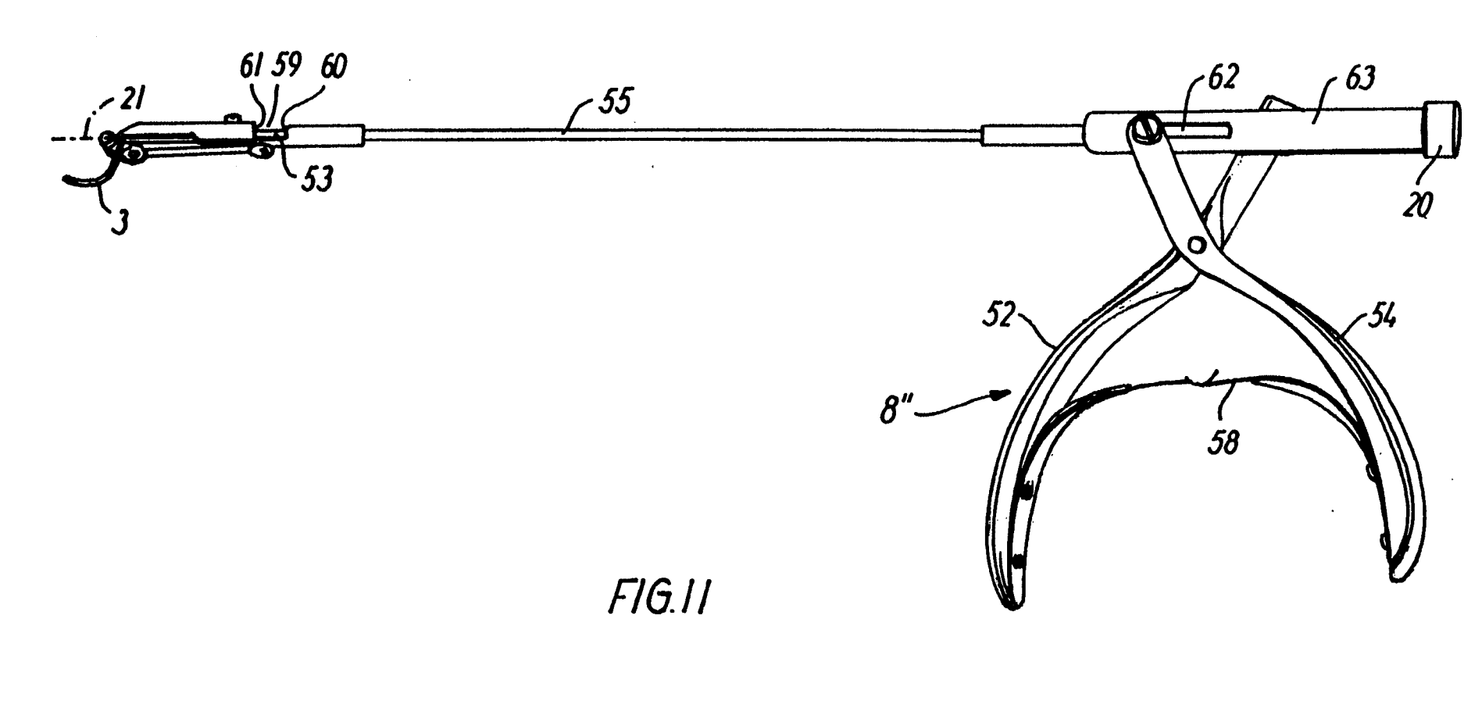
FIG. 11 is a side view of a prototype of a needle driving device according to the invention illustrating the needle holder in one extreme position.
Figures 12, 13:
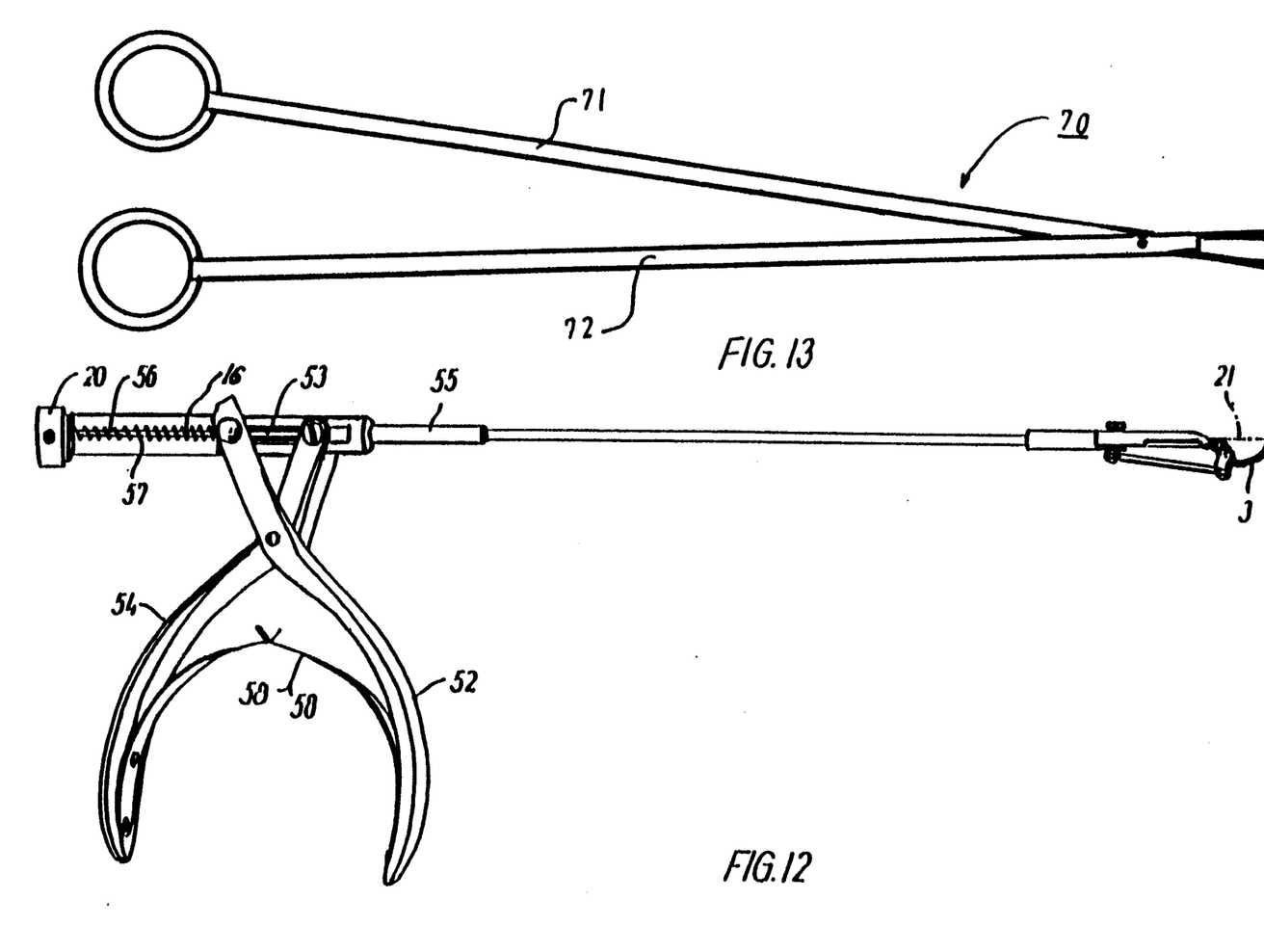
FIG. 12 is a side view seen from the opposite side of that illustrated in FIG. 11 and illustrating the needle holder pivoted to its other extreme position.
FIG. 13 is a perspective view of a gripping member in the form of a pair of tongs for gripping and extracting the needle.

FIGS. 11 and 12 illustrate a prototype of a needle driving device according to the invention. In FIG. 11 the needle holder is arranged in one extreme position in which the device is ready for use, the pointed end of the needle (not shown) being located substantially parallelly with the imaginary extension 21. In FIG. 12 the needle holder 3 is pivoted to its other extreme position past the imaginary extension line 21. The needle is pivoted by means of the handle 8". The one handle portion 52 is rigidly connected to a hollow tube 53, whereas the other handle portion 54 is connected to an outer tube 55 which may be displaced on the hollow inner tube 53. Inside the tube 53 a rod 16 is located which at its left-side end 56 is provided with a return spring 57 which ensures the return of the rod after a needle is pushed out of the needle holder 3. A spring 58 ensures that the two portions 52,54 of the handle are returned to the starting position illustrated in FIG. 11 after use of the needle driving device. The pivot movement is determined by adjusting the distance indicated at 59 and which is defined between an abutment 60 on the outer tube 55 and an abutment 61 connected to the the inner tube 53. In the handle a slot 62 is formed in a plate 63 which is tightly connected to the finger grip. The length of the slot 62 determines the travel of the finger grip 20 and hence defines the length by which a needle may be pushed through the needle holder 3.

Thus, FIGS. 11 and 12 illustrate the principle in which several mutually displacable tubes are used to effect the pivoting and needle driving by actuating the actuating members in or at the handle.

FIG. 13 shows gripping means 70 in the form of a pair of tongs. The tongs include elongated support members 71 and 72 which can be flexible pliable members or rigid, substantially rectilinear members. The tongs are used to grip and extract the needle into a position outside the surgical aperture or body cavity in a plate 63 which is tightly connected to the finger grip. The length of the slot 62 determines the travel of the finger grip 20 and hence defines the length by which a needle may be pushed through the needle holder 3.

Thus, FIGS. 11 and 12 illustrate the principle in which several mutually displacable tubes are used to effect the pivoting and needle driving by actuating the actuating members in or at the handle.

The set of tools being explained in connection with the drawing is used in the way explained in the introductory part of the specification seeing that also a gripping member is used, e.g. a pair of tongs being able to grip and pull out the needle when it is conducted through the tissues to be sutured. In an advantageous embodiment of the set of tools illustrated in FIGS. 1-8 the gripping member may advantageously be built together with the needle driving device 2' and be arranged so as to grip the needle immediately after it has been inserted through the tissue. Thus, the inner channel 52 of the scope may also be used for introduction of the thread conducting member to the point of operation.

I claim:

1. A set of tools for suturing in deep surgical apertures or body cavities, said set comprising:

a needle driving device having an elongated needle holder support member and a curved needle holder with a curved channel for accommodating a curved surgical needle provided with a thread, said needle holder being arranged at one end of the elongated needle holder support member, said needle driving device further including an elongated rod having a flexible foremost end attached to an end thereof for driving the needle out of the needle holder and being arranged within said elongated needle holder support member, and a gripping member for gripping and extracting the needle into a position outside the surgical aperture or body cavity and including an elongated support member, wherein the needle holder is mounted pivotally at said one end of the elongated needle holder support member, actuating means for pivoting the needle holder and the flexible foremost end of the elongated rod are provided at an opposite end of the elongated needle holder support member, and wherein the set of tools further comprises a thread conducting member having an elongated thread guide support member with two prongs arranged in a V-shape at one end thereof and a handle is provided at an opposite end thereof, and a thread guide is provided in a free end of each of the prongs and comprises means to guide said thread in the free end of each prong.

2. A set of tools according to claim 1, wherein the elongated support members of the needle driving device, the gripping member and the thread conducting member are flexible pliable members.

3. A set of tools according to claim 1, wherein the elongated support members of the needle driving device, the gripping member and the thread conducting member are rigid and substantially rectilinear members.

4. A set of tools according to claim 1, wherein the outer free end of the needle holder or the point of the needle in one extreme position of the needle holder, is arranged in a position at one side of a line extending in the longitudinal direction of the elongated needle holder support member and in the other extreme position is arranged in a position on the other side of said line, and that in said second extreme position the elongated rod is arranged to drive the needle completely out or approximately completely out of the needle holder.

5. A set of tools according to claim 4, wherein the needle holder has a curved channel having a radius of curvature and the elongated needle holder support member contains a channel for the elongated rod, said channel for the elongated rod having a curvature at an outermost end thereof which is defined by a radius of curvature which corresponds to the radius of curvature of an adjacent part of the curved channel of the needle holder, and that an axis of the pivoting of the needle holder is located in a plane extending perpendicularly to a center line through said channel for said elongated rod and through said channel of said needle holder and in close proximity to said center line.

6. A set of tools according to claim 5, wherein said plane is passed by the center line through the channel for said elongated rod and through said channel of said needle holder at a point where the channel of said elongated rod has an inflexion.

7. A set of tools according to claim 1, wherein the thread guides comprise a slot which is recessed in the free end of the prongs of the V-shape.

8. A set of tools according to claim 1, wherein the thread guides comprise an eye in the free end of each of the prongs of the V-shape.

9. A set of tools according to claim 1, wherein the actuating means are configured to be operated by a thumb and a forefinger and which are located in or at a handle intended to be maintained by the remaining three fingers of a user's hand.

10. A set of tools according to claim 1, wherein the gripping member is built together with the needle driving member and has a common elongated support member.

* * * * *